United States Patent [19]

Lehky et al.

[11] Patent Number: 4,511,734

[45] Date of Patent: Apr. 16, 1985

[54] PROCESS FOR THE PRODUCTION OF 3,3-DIMETHYLGLUTARIC

[75] Inventors: Pavel Lehky, Naters; Peter Hardt, Visp, both of Switzerland

[73] Assignee: Lonza Ltd., Gampel, Switzerland

[21] Appl. No.: 375,343

[22] Filed: May 5, 1982

[30] Foreign Application Priority Data

May 12, 1981 [CH] Switzerland .................. 3061/81

[51] Int. Cl.$^3$ .................. C07C 51/285; C07C 51/34; C07C 55/02
[52] U.S. Cl. .................. 562/524; 549/431; 562/577; 562/590; 562/593
[58] Field of Search .............. 562/590, 524, 528, 593, 562/577, 527; 549/431

[56] References Cited

U.S. PATENT DOCUMENTS

| | | | |
|---|---|---|---|
| 2,971,915 | 2/1961 | Borsoff et al. | 252/56 |
| 4,340,753 | 7/1982 | Cella | 562/528 |

FOREIGN PATENT DOCUMENTS 2813341 10/1978 Fed. Rep. of Germany.

OTHER PUBLICATIONS

Stoll et al., Helv. Chim. Acta, vol. 13, 1930, pp. 142–153.
W. T. Smith and G. L. McLeod, Org. Synthesis 31, 40 (1951).
F. B. Thole and J. F. Thorpe, J. Chem. Soc. 99, 422 (1911).
W. H. Perkin, Jr. and J. F. Thorpe, J. Chem. Soc. 75, 48, (1899).

*Primary Examiner*—Vivian Garner
*Attorney, Agent, or Firm*—Fisher, Christen & Sabol

[57] ABSTRACT

Process for the production of 3,3-dimethylglutaric acid from isophorone. In a first step the isophorone is converted with ozone into an ozone-addition product. The ozone-addition product is converted by hydrolysis into 3,3-dimethyl-5-oxohexanoic acid. The latter is converted into 3,3-dimethylglutaric acid by treatment with hydrogen peroxide.

10 Claims, No Drawings

PROCESS FOR THE PRODUCTION OF 3,3-DIMETHYLGLUTARIC

BACKGROUND OF THE INVENTION

1. Field of the Invention

The invention relates to a process for the production of 3,3-dimethylglutaric acid from isophorone.

2. Prior Art

Several methods are known from the literature for the production of 3,3-dimethylglutaric acid. Thus, according to W. T. Smith and G. H. McLeod, Org. Synthesis 31, 40 (1951), 3,3-dimethylglutaric acid is obtained by oxidation of dimedone (5,5-dimethyl-1,3-cyclohexanedione) with sodium hypochlorite. F. B. Thole and J. F. Thorpe, J. Chem. Soc. 99, 422 (1911) discloses obtaining 3,3-dimethylglutaric acid from acetone and cyanoacetamide. W. H. Perkin, Jr., and J. F. Thorpe, J. Chem. Soc. 75, 48 (1899), teaches producing 3,3-dimethylglutaric acid from dimethylacrylic ester and cyanoacetic ester.

All of these known processes have disadvantages, for example, they start out from expensive starting materials, pass over several synthesis steps, produce low yields, have large amounts of waste salt as a byproduct or produce a greatly contaminated end product.

BROAD DESCRIPTION OF THE INVENTION

It is an object of the invention to provide a process for the production of 3,3-dimethylglutaric acid, starting out from a cheap starting material, in a simple manner in high purity, so that no subsequent purifying processes have to be used. Other objects and advantages of the invention are set out herein or are obvious herefrom to one ordinarily skilled in the art.

The objects and advantages of the invention are achieved by the process and composition of the invention.

The process of the invention converts isophorone into an ozone-addition product, which is then converted into 3,3-dimethyl-5-oxo-hexanoic acid. From the latter, 3,3-dimethylglutaric acid is produced by means of hydrogen peroxide treatment.

The invention also includes a composition composed of isophorone and ozone.

3,3-dimethylglutaric acid and its esters are intermediate products in the production of pesticides (see German OS 28 13 341). Furthermore, they are useful as additives for lubricating oil (see U.S. Pat. No. 2,971,915).

DETAILED DESCRIPTION OF THE INVENTION

The invention involves the production of 3,3-dimethyl glutaric acid from isophorone, which has the formula:

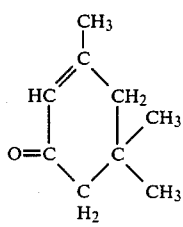

Isophorone is also termed isoacetophorone and 3,5,5-trimethyl-2-cyclohexen-1-one.

The conversion according to the invention can be carried out in a discontinuous or continuous manner. Preferably the first step, namely, the ozonization and the hydrolysis, for the 3,3-dimethyl-5-oxo-hexanoic acid is carried out continuously and the oxo-hexanoic acid is isolated. In an additional step the conversion to the end product is accomplished with $H_2O_2$.

The first step, the ozonization and hydrolysis, can be carried out without outside solvents or in the presence of outside solvents. Whenever one operates without outside solvents, then isophorone itself can serve as the solvent. Whenever outside solvents are used, then effectively alcohols, such as, methanol, ethanol and isopropanol, organic acids, such as, acetic acid and formic acid, esters, such as, ethyl acetate, halogenated hydrocarbons, such as, methylene chloride and carbon tetrachloride, and aliphatic, cycloaliphatic and aromatic hydrocarbons, such as, petroleum ether and cyclohexane, can be used as the solvent. These solvents can be used alone or in mixtures, for example, methanol and ethyl acetate or acetic acid and ethyl acetate.

The process of the invention, however can also be carried out in the presence of water. Since isophorone is not water soluble, it is present suspended in water and the reaction takes place in suspension.

The ozonolysis is carried out effectively at temperatures of $-80°$ to $+40°$ C. For practical reasons, advantageously a temperature of $-20°$ to $+20°$ C. is selected.

The reaction time depends essentially upon the performance of the ozone generator. Medium reaction times lie between about a few minutes and 6 hours.

The hydrolysis of the ozone addition product is carried out effectively with the help of hot, preferably boiling, water. The developing 3,3-dimethyl-5-oxo-hexanoic acid thereby will advantageously be isolated. The isolation can be achieved effectively by the addition of inorganic salts, such as, NaCl, KCl, phosphates and sulfates. Advantageously, the hydrolysis is carried out directly in the salt solution.

Subsequently, the 3,3-dimethyl-5-oxo-hexanoic acid is treated in a second step with $H_2O_2$. Advantageously, a 20 to 70 percent aqueous $H_2O_2$ solution is used for this, and one operates in the presence of a strong acid. As strong acids are those acids which are completely dissociated in the water. Advantageously, sulfuric acid and phosphoric acid are used.

The temperature which is used in the case of the $H_2O_2$-treatment is effectively 15° to 70° C., preferably 30° to 50° C.

For carrying out the reaction, a mixture of water, hydrogen peroxide and a strong acid is prepared in a first step by combining a solution of hydrogen peroxide, an acid or an aqueous solution of an acid and possibly water.

Hydrogen peroxide is used as an aqueous solution, wherein the concentration can vary within the wide range from 20 to about 85 percent. Industrially obtainable concentrations of 30 and 70 percent $H_2O_2$ in water are preferred.

The strong acid may be used in pure form or else as an aqueous solution. In the case where sulfuric acid is used as a strong acid, preferably industrial concentrated sulfuric acid is used.

The quantities and concentrations of hydrogen peroxide solution, of a strong acid and possibly of water are selected such that there are 5 to 10 moles of acid, 4 to 10 moles of hydrogen peroxide and 20 to 40 moles of water for 1 mole of 3,3-dimethyl-5-oxo-hexanoic acid.

A particularly advantageous ratio is 8 mole of sulfuric acid, 7 mole of hydrogen peroxide and 33 mole of water which is used for the oxidation of 1 mole of 3,3-dimethyl-5-oxo-hexanoic acid.

After completion of the reaction, the reaction solution is cooled down to a lower temperature, advantageously between −10° and 0° C., and the 3,3-dimethylglutaric acid which crystallizes out is separated. The thusly obtained 3,3-dimethylglutaric acid is pure and does not need to be specially purified.

By way of summary, 3,3-dimethylglutaric acid is obtained from isophorone by way of its ozonide, then 3,3-dimethyl-5-oxo-hexanoic acid, and treatment of the latter with $H_2O_2$.

As used herein, all parts, ratios, percentages and proportions are on a weight basis unless otherwise stated herein or otherwise obvious herefrom to one ordinarily skilled in the art.

EXAMPLE 1

1st Step

A solution of 200 g of isophorone in 1500 g of methanol was introduced during 16 hours from above into a bell bottom flask. Oxygen, which contains about 4 percent of ozone, was introduced from below. Thus, the liquid phase and the gaseous phase moved in counter current.

The flask was cooled on the outside by a cooling jacket, whereby the cooling medium was at 0° to 2° C. The solution running out below from the flask was introduced continuously into a solution of 82.5 g of primary sodium phosphate and 400 g of water. This aqueous phase was kept at 90° C. The methanol was distilled off continuously.

After completed ozonolysis, the phosphate solution was cooled to ambient temperature. The upper layer consisted of 258.5 g of moist 3,3-dimethyl-5-oxo-hexanoic acid; this moist product, according to gas chromatography, had a content of 88 percent, which corresponds to 227.5 g of a 100 percent product. This corresponds to a yield of 99.4 percent, related to the amount of isophorone used.

Only water was found as an impurity, which could be easily removed.

2nd Step 20 g of concentrated sulfur acid and 20.0 g of 30 percent of perhydrol were mixed while cooling. This mixture was cooled down to 30° to 35° C. For this purpose, 4.0 g of dimethyl-oxo-hexanoic acid were added drop by drop in such a way that the temperature remained at 35° C. After completion of the addition, the temperature was raised to 50° C. and kept at this temperature for 14 hours.

After completion of the reaction, the mixture solution was cooled to ambient temperature. The remaining peroxides were decomposed with sodium sulfite. The pH of the solution was adjusted to 1.5 with caustic soda. Then the reaction solution was extracted three times, always with 25 ml of ether. The ether phases were united, dried and evaporated to dryness. 3.97 g of a dimethylglutaric acid with a content of 82.6 percent was obtained. This corresponds to a yield of 81.8 percent, related to the amount of 3,3-dimethyl-oxo-hexanoic acid used.

EXAMPLE 2

1st Step

A suspension of 15.8 g of isophorone in 110 ml of water was cooled down to 0° C. Then a stream of oxygen which contains about 4 percent of ozone was introduced until the suspension was saturated with ozone. The entire matter was now heated to 95° C. and was boiled for 3 hours under reflux. The 3,3-dimethyl-5-oxo-hexanoic acid was subsequently isolated by evaporation of water under vacuum.

18.4 g of a light yellow liquid were obtained. This product, according to gas chromatography had a content of 92.3 percent, which corresponds to 16.9 g of a 100 percent product. This corresponds to a yield of 93.8 percent, related to the amount of isophorone used. Only water was found as an impurity, which could be removed easily.

2nd Step

The second step was conducted as in Example 1.

EXAMPLE 3

1st Step

A solution of 16 g of isophorone in 100 g of dichloromethane was cooled down to 0° C. A stream of oxygen, which contained about 4 percent of ozone, was conducted through this solution until the solution was saturated with ozone. Then the ozonolyzed solution was added drop by drop into 150 ml of boiling water, the dichloromethane was distilled off and the aqueous solution was boiled for another 3 hours. The 3,3-dimethyl-5-oxo-hexanoic acid formed was isolated by reducing under vacuum.

21.65 g of a yellowish liquid were obtained. This product, according to gas chromatography, had a content of 71 percent which corresponds to a yield of 85 percent related to the amount of isophorone used. The product which was still somewhat moist, could be used directly in the second step.

2nd Step

The second step was conducted as in Example 1.

EXAMPLE 4

1st Step

A solution of 28 g of isophrone in 250 g of formic acid was cooled down to 0° C. A stream of oxygen, containing about 4 percent of ozone, was conducted through this solution until the solution was saturated with ozone. Then the ozonolyzed solution was put into 100 ml of boiling water and was boiled for 2 hours reflux. Subsequently the hydrolyzate was concentrated in the rotational evaporator. 32.9 g of a yellow liquid was obtained which, according to gas chromatography, had a content of 81 percent of 3,3-dimethyl-5-oxo-hexanoic acid. This corresponds to a yield of 83.9 percent, related to the amount of isophorone used.

The formic acid and the water were removed by distillation from the raw product.

2nd Step

The second step was conducted as in Example 1.

EXAMPLE 5

1st Step

A solution of 4 g of isophorone in 40 g of glacial acetic acid was ozonized at 22° to 30° C. After the ozonolysis, 20 ml of water were added and the solution was heated for 3 hours to 80° C. and subsequently evaporated under the vacuum. 4.1 g of a yellow liquid was obtained which according to gas chromatography contained 81 percent of the 3,3-dimethyl-5-oxo-hexanoic acid. This corresponds to a yield of 72 percent, related to the amount of isophorone used.

2nd Step

The second step was conducted as in Example 1.

EXAMPLE 6

1st Step

The first step was conducted as in Example 1.

2nd Step

In a flask, cooled with cold water, 22.5 g of 85 percent phosphoric acid was combined with 14 g of 43 percent hydrogen peroxide. This mixture was heated to 50° C. Then 4 g of pure 3,3-dimethyl-5-oxo-hexanoic acid in 3.5 g of water was added drop by drop in such a way that the temperature remained between 50° to 55° C. Subsequently, the mixture was continued to be stirred overnight at 55° C.

After introduction of $SO_2$ for the destruction of the peroxide, the pH value was adjusted to 1.5 with concentrated NaOH, and was extracted three times with 50 ml of ether.

After evaporating the solution a crystal paste was obtained, which according to gas chromatography, consisted of 2.5 g (calculated as 100 percent) of 3,3-dimethylglutaric acid. This corresponds to a yield of 63.3 percent, related to the amount of 3,3-dimethyl-oxo-hexanoic acid used.

What is claimed is:

1. Process for the production of 3,3-dimethylglutaric acid from isophorone which comprises converting isophorone with ozone at a temperature of −20° to +20° C. in the presence of water or a solvent to an ozone-addition product, converting the ozone-addition product by hydrolysis in the presence or absence of a solvent into 3,3-dimethyl-5-oxo-hexanoic acid and converting the 3,3-dimethyl-5-oxo-hexanoic acid by treatment with hydrogen peroxide at a temperature of 15° to 70° C. into 3,3-dimethylglutaric acid.

2. Process as claimed in claim 1 wherein the solvent is an alcohol, an organic acid, an ester, a halogenated hydrocarbon, an aliphatic hydrocarbon, a cycloaliphatic hydrocarbon, an aromatic hydrocarbon or mixtures thereof.

3. Process as claimed in claim 1 wherein the hydrolyzed, ozone-addition product is isolated from solution by the addition of an inorganic salt to the solution.

4. Process as claimed in claim 1 wherein the hydrogen peroxide treatment is carried out in the presence of a strong acid.

5. Process as claimed in claim 4 wherein the strong acid is sulfuric acid or phosphoric acid.

6. Process as claimed in claim 1 wherein the product 3,3-dimethylglutaric acid is obtained by precipitation by cooling the reaction solution to a temperature of −10° to 0° C.

7. Process as claimed in claim 1 wherein the solvent is methanol, ethanol, isopropanol, acetic acid, formic acid, ethyl acetate, methylene chloride, carbon tetrachloride, petroleum ether, cyclohexane or mixtures thereof.

8. Process as claimed in claim 1 wherein the hydrolysis is achieved by means of hot water or an aqueous solution of an inorganic salt.

9. Process as claimed in claim 8 wherein the inorganic salt is NaCl, KCl, a phosphate or a sulfate.

10. Process as claimed in claim 8 wherein the hydrolysis is achieved by means of an aqueous solution of an inorganic salt.

* * * * *

UNITED STATES PATENT OFFICE
CERTIFICATE OF CORRECTION

Patent No. 4,511,734    Dated April 16, 1985

Inventor(s) Pavel Lehky and Peter Hardt

It is certified that error appears in the above-identified patent and that said Letters Patent are hereby corrected as shown below:

On the title page, Item (54) should read;

-- [54] PROCESS FOR THE PRODUCTION OF 3,3-DIMETHYLGLUTARIC ACID --.

Signed and Sealed this

Twenty-seventh Day of August 1985

[SEAL]

Attest:

DONALD J. QUIGG

Attesting Officer    Acting Commissioner of Patents and Trademarks